United States Patent [19]

Anis

[11] Patent Number: 4,602,630
[45] Date of Patent: Jul. 29, 1986

[54] RADIAL KERATOTOMY KNIFE

[76] Inventor: Aziz Y. Anis, 7531 N. Hampton, Lincoln, Nebr. 68506

[21] Appl. No.: 734,886

[22] Filed: May 16, 1985

[51] Int. Cl.$^4$ ............................................. A61F 17/32
[52] U.S. Cl. ...................................... 128/305; 30/286
[58] Field of Search ............... 128/305, 314, 311, 313; 30/294, 286, 287, 353

[56] References Cited

U.S. PATENT DOCUMENTS

| 3,712,293 | 1/1973 | Mielke | 128/305 |
| 4,324,044 | 4/1982 | Shahinian | 128/305 |
| 4,520,815 | 6/1985 | Marinoff | 128/305 |

FOREIGN PATENT DOCUMENTS 8501431  4/1985  European Pat. Off. ............ 128/305

*Primary Examiner*—Robert Peshock
*Assistant Examiner*—John G. Weiss
*Attorney, Agent, or Firm*—Zarley, McKee, Thomte, Voorhees & Sease

[57] ABSTRACT

A radial keratotomy knife comprising an elongated handle having a flat depth gauge or guard mounted at one end thereof and having an elongated opening formed therein. A flat surgical blade is mounted on the handle and has a cutting edge extending through the elongated opening in the guard. The guard has a width and length sufficient to cause the cornea of the eye to be flattened during the surgical procedure so that uniform radial incisions may be made in the cornea during the surgical procedure.

4 Claims, 7 Drawing Figures

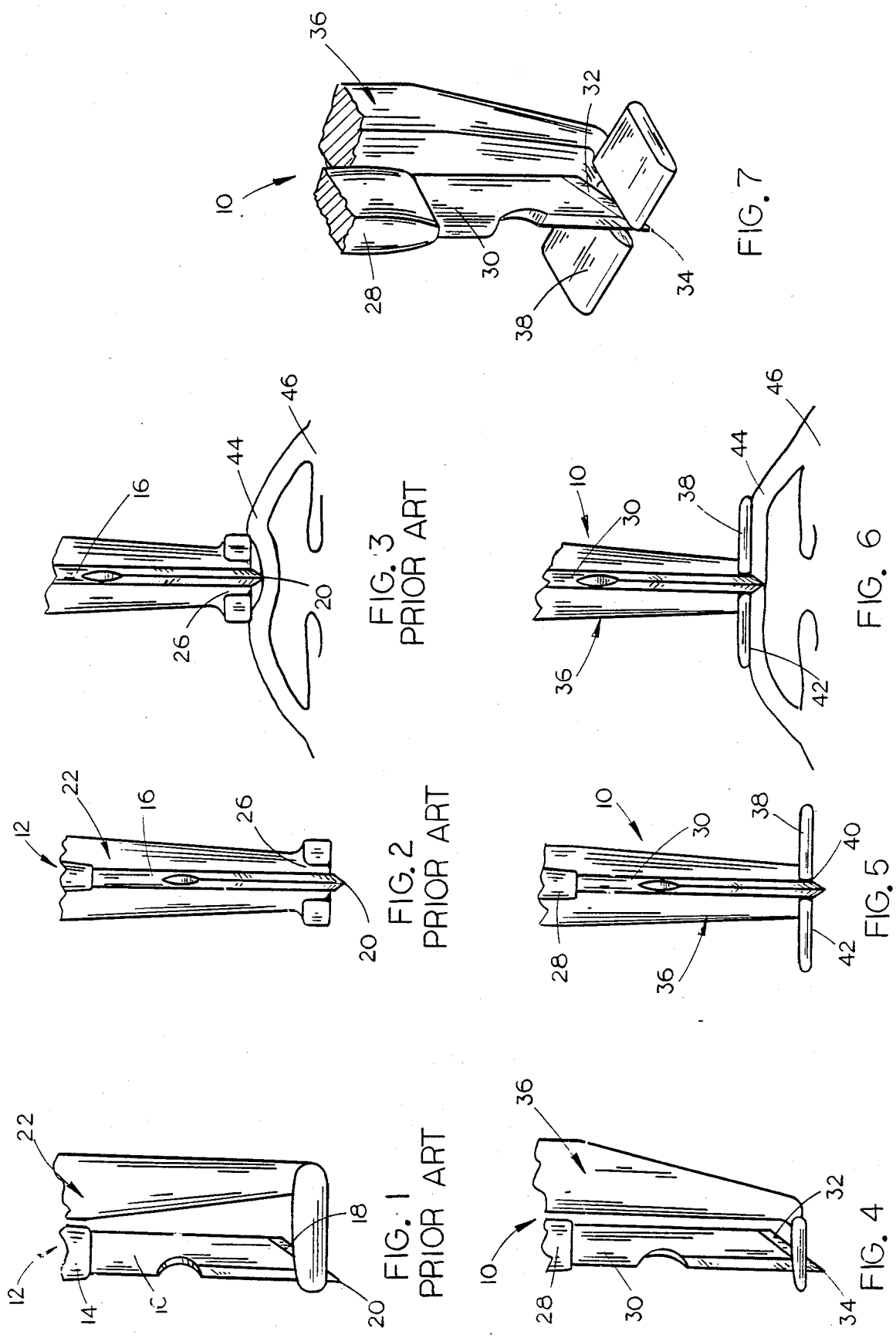

RADIAL KERATOTOMY KNIFE

BACKGROUND OF THE INVENTION

This invention relates to a radial keratotomy knife and more particularly to a radial keratotomy knife having a depth gauge or guard mounted thereon.

Radial keratotomy knives normally consist of a handle having a surgical blade extending therefrom which is used to make a plurality of radially extending incisions in a patient's cornea. It is extremely important that the depth of the incisions be controlled and that all of the incisions have a uniform depth. In an effort to control the depth of the incision created by the radial keratotomy knives, a guard or depth gauge has been previously provided and the same is depicted in the drawings and identified as "Prior Art". In the prior art knife, the guard or depth gauge is quite narrow which results in the cornea being deformed as illustrated in FIG. 3. The deformation of the cornea as illustrated in FIG. 3 results in inaccurate incisions being created. Further, the opening formed in the guard of the prior art knife, through which the blade extends, is substantially greater than the thickness of the blade which can sometimes result in the cornea protruding upwardly through the opening which also results in non-uniform and inaccurate incisions being created.

It is therefore a principal object of the invention to provide an improved radial keratotomy knife.

A further object of the invention is to provide an improved radial keratotomy knife having a flat guard or depth gauge provided thereon which has a sufficient length and width so as to achieve proper incisions.

A further object of the invention is to provide an improved radial keratotomy knife including a guard having an elongated opening formed therein through which the knife blade extends with the width of the elongated opening being just slightly larger than the thickness of the knife blade to prevent the cornea from protruding upwardly therethrough during the surgical procedure.

These and other objects will be apparent to those skilled in the art.

BRIEF DESCRIPTION OF THE DRAWINGS

FIG. 1 is a partial side view of a prior art knife:

FIG. 2 is a partial side view of the knife of FIG. 1:

FIG. 3 illustrates the knife of FIG. 2 being used to create an incision in a cornea of an eye:

FIG. 4 is a partial side view of the knife of this invention:

FIG. 5 is a partial side view of the knife of FIG. 4 as viewed from the left of FIG. 4:

FIG. 6 illustrates the knife of FIGS. 4 and 5 being used to create an incision in the cornea of an eye; and FIG. 7 is a perspective view of the knife of this invention.

SUMMARY OF THE INVENTION

A radial keratotomy knife is described comprising an elongated handle portion having a flat depth gauge mounted at one end thereof and having an elongated opening formed therein at the center thereof. The depth gauge has a lower surface portion which is adapted to engage the exterior surface of the patient's cornea. A flat surgical blade is secured to the handle and extends therefrom through the elongated opening in the depth gauge so that a predetermined portion of the cutting edge of the blade is disposed below the lower surface of the gauge.

DESCRIPTION OF THE PREFERRED EMBODIMENT

The numeral 10 refers to the radial keratotomy knife of this invention while the numeral 12 refers to a prior art radial keratotomy knife. The prior art knife 12 includes a handle portion 14 having a flat surgical blade 16 secured thereto and extending therefrom. As seen in the drawings, the blade 16 includes a cutting edge 18 having a tip 20. A guard or depth gauge 22 is secured to the handle portion 12 and has an elongated slit or opening 26 formed therein through which the blade 16 extends. As seen in FIG. 2, the width of the opening 26 is considerably greater than the thickness of the blade 16 which can cause the cornea to protrude upwardly through the opening 26 during the surgical procedure. The primary drawback to the prior art knife 12 is that it does not have a sufficient width which causes the cornea to be deformed during the surgical procedure as illustrated in FIG. 3.

Knife 10 includes an elongated handle portion 28 having a flat surgical blade 30 extending therefrom which has a cutting edge 32 and a tip 34. Guard or depth gauge 36 is secured to handle portion 28 and has an opening 40 formed therein. The width of opening 40 is slightly greater than the thickness of the blade 30 so that objectionable protrusion of the cornea upwardly through the opening 40 during the surgical procedure is prevented. Preferably, guard 36 has a width of approximately 5½ millimeters and a length of approximately 1½ to 2 millimeters. The design of the guard 36 is such that a very wide cornea engaging surface 42 is provided so that the cornea 44 of the eye 46 will be flattened during the surgical procedure so that a uniform incision depth is achieved.

Thus it can be seen that the knife of this invention accomplishes at least all of its stated objectives.

I claim:

1. A radial keratotomy knife, comprising,
   an elongated handle portion having opposite ends,
   a flat depth gauge means mounted on said handle portion at one end thereof and having an elongated opening formed therein at the center thereof, said depth gauge means having a lower surface portion adapted to engage the exterior surface of the patient's cornea,
   a flat surgical blade having a cutting edge,
   said blade secured to said handle portion at said one end thereof and extending therefrom through said elongated opening so that a predetermined portion of said cutting edge is disposed below said lower surface of said depth gauge means,
   said depth gauge means having a width which is substantially greater than its length.

2. The knife of claim 1 wherein the thickness of said blade is substantially equal to the width of said elongated opening.

3. The knife of claim 1 wherein said depth gauge means comprises a pair of flat wing portions having said elongated opening positioned therebetween.

4. The knife of claim 1 wherein said depth gauge means has a width of approximately 5½ millimeters and a length of approximately 1½ to 2 millimeters.

* * * * *